(12) United States Patent
Engel et al.

(10) Patent No.: US 10,354,438 B2
(45) Date of Patent: Jul. 16, 2019

(54) ILLUMINATION IN RENDERING OF ANATOMY WITH FUNCTIONAL INFORMATION

(71) Applicant: Siemens Healthcare GmbH, Erlangen (DE)

(72) Inventors: Klaus Engel, Nürnberg (DE); James Williams, Knoxville, TN (US)

(73) Assignee: Siemens Healthcare GmbH, Erlangen (DE)

( * ) Notice: Subject to any disclaimer, the term of this patent is extended or adjusted under 35 U.S.C. 154(b) by 335 days.

(21) Appl. No.: 14/843,347

(22) Filed: Sep. 2, 2015

(65) Prior Publication Data

US 2017/0061681 A1    Mar. 2, 2017

(51) Int. Cl.
| | |
|---|---|
| *A61B 5/055* | (2006.01) |
| *G06T 15/50* | (2011.01) |
| *A61B 6/00* | (2006.01) |
| *G06T 15/06* | (2011.01) |
| *G06T 15/00* | (2011.01) |
| *A61B 5/00* | (2006.01) |

(52) U.S. Cl.
CPC .......... *G06T 15/506* (2013.01); *A61B 5/0035* (2013.01); *A61B 6/5211* (2013.01); *A61B 6/5235* (2013.01); *G06T 15/005* (2013.01); *G06T 15/06* (2013.01); *A61B 5/055* (2013.01); *A61B 6/461* (2013.01); *G06T 2210/41* (2013.01); *G06T 2215/16* (2013.01)

(58) Field of Classification Search
CPC ......... A61B 5/055; A61B 6/032; A61B 6/037; A61B 6/461; A61B 6/5211; G06T 15/005; G06T 15/06; G06T 15/506; G06T 2210/41; G06T 2215/16

See application file for complete search history.

(56) References Cited

U.S. PATENT DOCUMENTS

| | | | |
|---|---|---|---|
| 9,001,124 B2 | 4/2015 | Engel | |
| 9,330,485 B2 | 5/2016 | Wahrenberg | |
| 2011/0069070 A1 | 3/2011 | Engel | |
| 2016/0343161 A1* | 11/2016 | Paladini | .................. G06T 15/08 |

FOREIGN PATENT DOCUMENTS

| | | |
|---|---|---|
| CN | 102024269 A | 4/2011 |
| CN | 102024271 A | 4/2011 |
| CN | 104008568 A | 8/2014 |
| CN | 101178814 A | 5/2018 |

OTHER PUBLICATIONS

Kroes, T., Post, F., Botha, C., "Exposure Render: An Interactive Photo-Realistic Volume Rendering Framework", pp. 1-10, vol. 7 No. 7, Jul. 2012.

(Continued)

*Primary Examiner* — Mark D Remaly

(57) ABSTRACT

Functional and anatomical information are combined in medical imaging. The functional information is treated as a light source illuminating surrounding anatomy, not just along a viewing direction. As a result, rendered images of the anatomy include highlighting or visual lighting queues showing locations of biological activity using global illumination.

11 Claims, 2 Drawing Sheets

(56) References Cited

OTHER PUBLICATIONS

Ropinski, T., Döring, C., Rezk-Salama, C., "Interactive Volumetric Lighting Simulating Scattering and Shadowing", pp. 169-176, Mar. 2010.
Rezk-Salama, C., "GPU-Based Monte-Carlo Volume Raycasting" Computer Graphics Group, University of Siegen, Germany, pp. 411-414, 2007.
U.S. Appl. No. 14/719,469, filed May 22, 2015.
Chinese Office Action dated Sep. 3, 2018 in corresponding Chinese Patent Application No. 201610773703.7.
Guifen, Lin, et al., "3-D PET Image Reconstruction Based on Monte-Carlo Simulation", Atomic Energy Science and Technology, vol. 42 ,No. 12, Dec. 2008.
Zheng, Ling, et al., "Using global illumination in volume visualization of rheumatoid arthritis CT data", CPEL1652444, Nov. 14, IEEE Computer Society, 0272-1716/14, IEEE Computer Graphics and Applications.
Chinese Office Action dated May 22, 2019 in corresponding Chinese Patent Application No. 201610773703.7.
Fu, Yin et al; "Subjective assessment and perception model of PET/CT image quality"; in Journal of Shenzhen University Science and Engineering; pp. 205-212; Mar. 2015.
Wenhua, Wang et al; "PET-CT Multimodal Volume Rendering Designed using dual transfer functions"; in Computer Applications and Software; vol. 30; No. 10; Oct. 2013.

\* cited by examiner

ILLUMINATION IN RENDERING OF ANATOMY WITH FUNCTIONAL INFORMATION

BACKGROUND

The present embodiments relate to medical imaging. Three-dimensional (3D) visualization is a common practice to assess and record the internal conditions of patients. Both anatomical and functional information may be available for visualization. Functional information represents biological activity and is from molecular imaging modalities like positron emission tomography (PET) or single-photon emission computed tomography (SPECT). Anatomical information is available from other modalities, such as computed tomography (CT) or magnetic resonance imaging (MRI).

Conventionally, PET and SPECT information is fused with CT and MRI volume data, showing functional information as colored blobs using a color palette for increased metabolism. The color palette may range from yellow for medium to red for high metabolism. In a conventional ray-casting algorithm, the color emission from voxels of the PET and SPECT data is derived from the intensity of the measured functional activity. When visualizing functional information together with registered anatomical information, the functional information should be clearly visible, showing areas of increased biological activity within the anatomical context. Clear viewing of the functional information might be difficult, since anatomical features often occlude the functional information. For example, a tumor with greater biological activity is embedded in an organ, so the anatomical representation of the organ blocks viewing of the embedded functional information.

The occlusion may be avoided, at least in part. Since the emitted color for the functional information is only transported on a direct path from the emitting point to the image plane pixel in ray casting approaches, the transfer function for the anatomy information is set in a way that bones are opaque while soft tissue is transparent. Alternatively, cut planes are employed to remove occluding anatomy. Both approaches result in less anatomical information.

BRIEF SUMMARY

By way of introduction, the preferred embodiments described below include methods, systems, instructions, and computer readable media for medical imaging of functional and anatomical information. The functional information is treated as a light source illuminating surrounding anatomy, not just along a viewing direction. As a result, rendered images of the anatomy include highlighting or visual lighting queues showing locations of biological activity.

In a first aspect, a system is provided for medical imaging of functional and anatomical information. An emission imaging system is configured to measure the functional information representing a volume of a patient. A medical imager is configured to measure the anatomical information representing the volume of the patient. A graphics rendering processor is configured to render an image of the volume of the patient from the anatomical information with global illumination. The global illumination is based on the functional information. A display is configured to display the image.

In a second aspect, a method is provided for medical imaging of functional and anatomical information. Generation of light by detected emissions within a patient volume is modeled. Anatomy of the patient volume is rendered using the modeling of the light generation by the detected emissions. An image resulting from the rendering is displayed.

In a third aspect, a non-transitory computer readable storage medium has stored therein data representing instructions executable by a programmed processor for medical imaging of functional and anatomical information. The storage medium includes instructions for generating a three-dimensional image of anatomy of a patient, adding lighting emanating in multiple directions from parts of the anatomy from which function is detected to the three-dimensional image, and displaying the three-dimensional image.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Realistic lighting (e.g., the presence of global illumination effects such as ambient occlusion, shadows, and/or light bleeding) is an important clue for depth and shape perception. Consequently, it is important to provide such lighting effects when rendering images from volume data to allow better image understanding. In the medical domain, lighting may supply shape and depth information for better 3D image understanding and improve the image quality for noisy and low-dose volume reconstructions, such as for functional information.

Anatomical volume data is illuminated using functional volume data. A physically-based volume rendering approach is used to visualize the anatomical data. The physically-based volume rendering simulates various paths from light to a detector, so supports global illumination effects. The functional data is used to define light emitting voxels or light source positions or regions. Instead of emitting light from areas with high metabolism solely towards the camera, the light is transported to the surrounding tissue and illuminates the anatomy using global illumination effects. By using the functional data to define light, glowing hot spots of areas with increased metabolism are provided in the rendering of the anatomy. The color and intensity of the glowing hot spots are determined by the measured functional information from PET or SPECT data.

Figure 1:
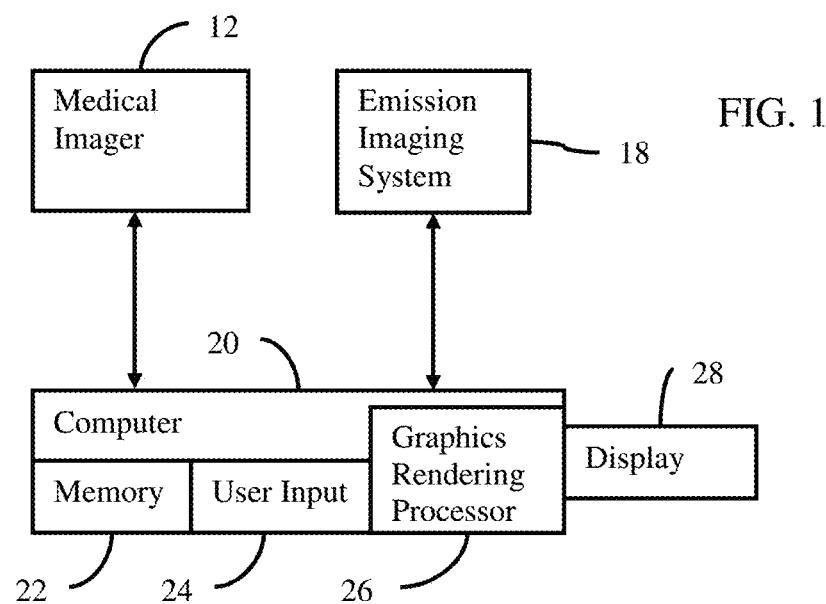
FIG. 1 is a block diagram of one embodiment of a system for medical imaging from anatomical and functional information.

FIG. 1 shows one embodiment of a system for medical imaging of functional and anatomical information. The system is configured to implement the method of FIG. 3 or other methods. The system renders a 2D image representing 3D space or a volume of a patient (i.e., renders a 3D image). The image is rendered using both functional and anatomical information. Rather than reduce or remove anatomical information to avoid occlusion of functional information, the functional information is used as a global illumination source. Instead of the traditional way of rendering potentially occluding anatomy with a color blob, the functional information is indicated as a glowing hot spot or light.

The system provides an image or images used for diagnosis. Additionally, there are applications for photorealistic medical volume rendering in augmented reality, marketing, doctor-patient communication, and anatomical education. Other applications may exist.

The system is shown with three components, the medical imager 12, the emission imaging system 18, and the computer 20. These three components are separate devices. In other embodiments, the computer 20 is part of either of the medical imager 12 or the emission imaging system 18. In yet other embodiments, the computer 20 is provided as a workstation, server, or computer without the medical imager 12 or the emission imaging system 18. The anatomical and functional information are stored in the memory 22. In yet another embodiment, the medical imager 12 is a CT system integrated with the emission imaging system 18, and the computer 20 is a controller or integrated computer of the emission imaging system 18. Additional, different, or fewer components may be provided, such as including other or different sources of anatomical or functional information.

The medical imager 12 is a CT, MRI, ultrasound, x-ray, or fluoroscopy system. The medical imager 12 is any now known or later developed medical imaging system for scanning an interior of the patient and imaging anatomy. In one embodiment, the medical imager 12 is a CT system. An x-ray source and opposed detector are mounted to a gantry. The gantry moves the source and detector about a patient, providing projected measures of x-ray attenuation from various angles relative to the patient. A processor or computer reconstructs the patient anatomy from the measures using computed tomography. In another embodiment, the medical imager 12 is a MRI system. A main magnet generates a $B_0$ field. Gradient coils spatially encode magnetic resonance response of molecules in the patient to magnetic pulses provided by a whole body or local coil or coils. The same or different coils measure the response to the magnetic pulses, providing k-space data. A processor or computer applies a Fourier or other transform to convert the k-space data into measures representing anatomy of the patient.

The medical imager 12 measures anatomical information representing the volume of the patient. The medical imager 12 is configured to scan an internal region of the patient. Any portion or extent of the patient may be scanned, such as a scan of an organ, torso, extremity, or full body. The scan acquires data representing the interior of the patient. The represented portion includes a volume or three-dimensional distribution of response from the patient.

The medical imager 12 acquires at least one set of data. The set or frame of data represents the internal region of the patient at a specific time or period. A static volume is acquired. Alternatively, the scanning is repeated or performed in an ongoing manner to acquire a sequence of sets of data. Each set represents the volume at a given time or period, so the sequence represents the volume over time (3D+t or 4D data). Any frame or volume rate may be provided.

The anatomical information or scan data is reconstructed to a uniform grid (e.g., a 3D reconstruction) or has another format representing the volume. In one embodiment, the data from the scan is formatted as voxels in an isotropic grid. For example, voxels in a 512×512×512 Cartesian grid are used. Anisotropic grids may be used. Other formats may be used, such as the data representing locations in a polar coordinate format. For each voxel or location, a scan response is provided by a scalar value (e.g., 16 bit dynamic range), but other representations may be used, such as RGB values. The scalar values of the voxels are measurements of the anatomy of the patient.

The emission imaging system 18 is a PET, SPECT, or other molecular or functional imaging system. The emission imaging system 18 measures biological activity, so may be a MRI or CT system configured to measure function rather than or in addition to anatomical information. In one embodiment, the emission imaging system 18 is a PET system. A cylinder or other arrangement of detectors defines a patient or emission detection space. A radioactive tracer in the patient causes emissions to occur. The tracer bonds to or interacts with locations of biological activity. The detectors detect each emission from the tracer at two points. A computer or processor reconstructs the locations or points of emissions from many detections. In another embodiment, the emission imaging system 18 is a SPECT system. A gamma camera is rotated about a patient detecting emissions from a tracer. A computer or processor reconstructs the locations or points of emission from the detections.

The emission imaging system 18 measures the function within a volume of the patient. The measurements are for the same or overlapping volume for which the medical imager 12 acquires data. The measurements are formatted as voxels in a same or different grid than the anatomical information. The voxels represent detected emissions from the tracer in the patient, so provide functional information for the patient. The emission imaging system 18 measures biological activity in the volume.

The computer 20 is a tablet, personal computer, lap top, server, workstation, controller, or other device for generating medical images. The computer 20 includes a memory 22, a user input 24, a graphics rendering processor 26, and a display 28. Additional, different, or fewer components may be provided, such as not having the user input 24.

The computer 20 uses the anatomical information from the medical imager 12 and the functional information from the emission imaging system 18 to render a 3D image or a 2D representation of a volume. In one embodiment, the memory 24 stores the anatomical information, functional information, rendered image, lighting model, paths, transfer functions, and/or rendering information.

The memory 24 is a graphics processing memory, video random access memory, random access memory, system memory, cache memory, hard drive, optical media, magnetic media, flash drive, buffer, database, combinations thereof, or other now known or later developed memory device for storing the set or sets of voxel data or other data.

The computer 20 is configured by software, firmware, and/or hardware to render. The memory 24 stores instructions for the computer 20 or graphics rendering processor 26 to perform rendering. The memory 24 or other memory is a non-transitory computer readable storage medium storing data representing instructions executable by the programmed processor 26 for medical imaging. The instructions for implementing the processes, methods, and/or techniques discussed herein are provided on computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The user input 24 is a keyboard, button, slider, knob, track pad, mouse, touch sensor, touch screen, or other sensor. The user input 24 is configured to receive input from the user. The input may configure the images for viewing, such using a slider or click-and-drag operation to rotate a view or set a window level. In one embodiment, the user input 24 receives user selection of a level of illumination. A base brightness and/or illumination color map is selected by the user. Alternatively, the computer 20 uses a default level of illumination and/or color map (e.g., transfer function).

The graphics rendering processor 26 is a general processor, central processing unit, control processor, graphics processor, graphics processing unit, graphics card, digital signal processor, three-dimensional rendering processor, image processor, application specific integrated circuit (ASIC), field programmable gate array (FPGA), digital circuit, analog circuit, combinations thereof, or other now known or later developed device for rendering an image from data. The graphics rendering processor 26 is a single device or multiple devices operating in serial, parallel, or separately.

The graphics rendering processor 26 is configured by software, firmware, and/or hardware to render a 3D image or other 2D display representation of a volume. The image is a single representation of the patient volume from a viewpoint and view direction. Projection or surface rendering may be used. For projection rendering, the graphics rendering processor 26 cast rays through the volume. A ray is cast for each pixel of the image. In one embodiment, the rendering uses a physically-based volume rendering. For example, Monte Carlo rendering or path tracing is used. Paths are traced through the volume. The paths may not be straight lines of rays. The paths may follow routes taken by light to reach a pixel in a projection or detector plane, such as accounting for any number of reflections, bounces, refractions, and/or scattering. Any number of paths may be traced for each pixel. The physical structure or anatomy information may be used to randomly or probabilistically determine scattering or path divergence for the physically-based volume rendering. Natural shading, physically based volume rendering, and light maps may be employed for rendering. Approaches capable of incorporating global illumination other than path tracing may be used, such as photon mapping, bidirectional path tracing or metropolis light transport.

The image is rendered using the anatomical and functional information, such as the sets of voxels representing the anatomy and function in a same volume or overlapping volumes. The rendering is of the volume of the patient and from the anatomical information. The voxels representing anatomical information are used to render the image. The base color and/or opacity for each voxel are determined by application of a transfer function to the anatomical information.

The functional information is used for illumination or lighting. For local illumination, surfaces or opaque structure is determined. The light along a ray from a light source at the surface is computed. For environmental lighting, an external light source or sources are modeled. The external light source is virtual or may be based on measures in the patient environment, such as being measures of ambient light. In one embodiment, global illumination is used. Global illumination provides for light glowing or passing through soft tissue. Global illumination accounts for indirect lighting, such as provided by scattering of light as sourced within the patient volume. Path tracing is used for the indirect lighting or lighting along indirect or bouncing paths. Combinations of different lighting may be used, such as global illumination and environmental lighting.

The global illumination or other lighting is based on the functional information. The functional information is treated as a light source and/or interacts with lighting differently than the anatomical information. For example, locations or voxels with functional measurements above a threshold are treated as sources of illumination from within the volume. The locations are point sources radiating light to the surrounding tissue. As a result, the light from the locations is transported to surrounding anatomy locations spaced from a ray line from a virtual viewer (i.e., camera) to a pixel location on a detector plane for rendering. The anatomy is used for rendering, but the functional information is used for global illumination in the rendering of the anatomy. This causes the anatomy at locations of biological activity to glow, shine, or be highlighted due to lighting relative to locations of low or no biological activity. This also causes anatomy near locations of biological activity to have lighting cues (e.g., shadows or shading).

The graphics rendering processor 26 accesses the memory 22 for the anatomical and functional information. The user input 24 provides user control information for rendering, such as selection of a window or level, transfer function, view direction, zoom, and/or other input. Alternatively, default values or use-selected values are stored in the memory 22 and accessed from the memory 22.

In one embodiment, the graphics rendering processor 26 renders with a strength of the lighting (e.g., global illumination) being based on a control input from the user. The global strength of the functional information-based lighting may be influenced or set by the user using a user interface control, such as a slider. Alternatively, the strength is based on a default value. The strength may define a mean, median, or dynamic range of lighting intensity. By adjusting the strength, the mapping of the functional information to light intensity is altered to provide more or less lighting intensity for a given scalar value.

In one embodiment of rendering, the graphics rendering processor 26 accumulates the base color and opacity along one or more paths to a pixel or image plane location. Monte Carlo or other path tracing defines one or more paths to each pixel. For each pixel, the color is accumulated from the path or paths. The voxels along the path are accumulated by averaging or summing the mapped colors and opacities. The anatomical information is used to render a color weighted by opacity for each pixel.

Each voxel scalar or anatomy sample maps to a color (e.g., RGB value) and opacity. A transfer function for the anatomy sets the relationship of the scalar to the color and opacity. In a path-tracing rendering, such as the Monte Carlo rendering, a sample from the anatomical volume data is computed for each sample point along each path during ray marching. The sample from the anatomical volume data is mapped to color and opacity using the transfer function. The color and opacity from the anatomy transfer function is assigned to the sample position as the base color and opacity value.

The lighting contributes to the anatomical rendering. The opacity for each voxel or location is accumulated along the path to compute the probability of a light scattering event, such as in woodcock tracking. Using random number generation, the existence of a scattering event is determined from the probability. Where no scatter event occurs, the accumulation along the path continues.

Where a scatter event occurs, the base color for the sample at the location of occurrence and/or the accumulated color along the path to the location of occurrence are modified. The anatomy color is modified with a light color and/or light intensity. Sample from the functional volume data are computed for sample points along each path during ray marching. The functional samples are mapped from the functional information for the respective locations to light colors or spectrums and light intensities with a functional transfer function. Any transfer function may be used. In one embodiment, the greater scalar representing greater biological activity maps to a white or red color, and lesser scalar maps to a yellow, blue, gray, black, or other color.

The color is used to modify the paths light color at each scattering event. Where scattering occurs, light is added to the location based on the functional sample at that location or accumulation of functional samples along the path. This results in the location being a light source. Light is added to the voxel by adding the light color and/or intensity. To add light, the color from the anatomical sample or accumulated sample is modified, such as being tinted and/or changed in brightness. Color shading and/or intensity is varied to account for the added light.

Figure 2:
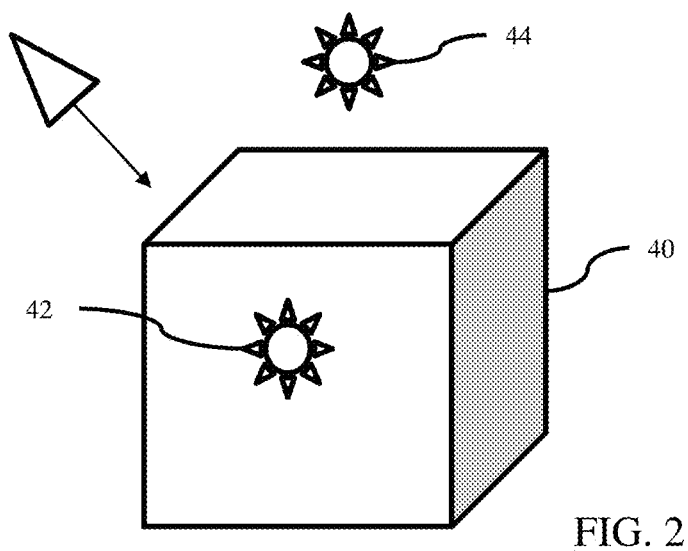
FIG. 2 illustrates lighting modeled from functional information in a volume.

FIG. 2 represents an example where the viewer is viewing a volume 40. Within the volume, a spherical region 42 has functional measures above a threshold. Those measures result in the voxels therein being light sources radiating light in various directions. The viewer views the volume 40 from a direction, represented by the arrow. The light radiates in parallel and not in parallel with the viewing direction. Using global illumination and Monte Carlo path tracing, the volume 40 may be rendered to show the anatomy at voxels associated with the biological activity highlighted as brighter, tinted, and/or otherwise glowing as light sources. Anatomy for other voxels adjacent to and spaced from the light source are likewise modified to account for the lighting. Additional environmental lighting 44 may also be added.

Various approaches may be used to add the lighting derived from the functional data. For example, the base color and/or opacity for the base sample from anatomy for the location are modified. As another example, lighting along the path is accumulated and added to a final accumulated pixel color for the anatomy resulting from accumulation along the path.

Any modification may be provided. In one embodiment, the light for each sample is multiplied or used to weight the color from anatomy for that sample. For example, RGB of the base color are weighted with light RGB values. In another embodiment, environmental lighting is handled as a weight. The light modeled as global illumination is added, such as summing the base RGB value with the light RGB values from the functional data.

In one approach, the light color and light intensity from the functional data is added as having an emissive property at the location. The light color and intensity are added to an emissive property or properties of the sample point and added to the path's light contribution. Any emissive property may be used, such as shading, reflection, refraction, or illumination. The sampling of the path is continued until the tracing of the path is completed and the light contribution is added to the virtual detector pixel of the image plane. The emissive contribution of each sample point along the path with a functional sample is added or accumulated. Upon exiting the volume by a path, the accumulated anatomical information is modified by the accumulated color. Since the paths follow light interaction, a pixel includes lighting contribution from surrounding voxels relative to a straight ray line. Other lighting, such as from the environment, may also be added or used to modify.

In another approach, the path tracing in the rendering terminates at a location along the path. The path is terminated once a certain light intensity from the functional sample point is found or computed. Once terminated, the light color and light intensity are added to results of the accumulation of anatomy samples for the path as terminated. The light contribution of the light source defined by the functional data is directly added to the detector pixel of the image plane. The hotspot given as the location with the light intensity above a threshold or for accumulated light intensity above a threshold terminates the path tracing. The accumulated anatomy color is modified by the light intensity upon termination without other lighting (e.g., without environmental lighting).

After determining the color for each pixel on the detector plane, an image is generated. The image shows hotspots or locations with greater lighting while still providing anatomical information. The global illumination based on the functional information highlights the anatomy associated with greater biological activity, such as with lighting cues for adjacent anatomy.

For further emphasis, a sequence of images may be generated. The volumes or data used for the sequence are static or the same for each image. The strength of the global illumination varies, such as varying in a cyclical pattern, over the sequence. This results in the hotspots or locations of biological activity appearing to pulsate with corresponding lighting cues for adjacent anatomy when the images of the sequence are displayed over time. The locations of biological activity may be better recognized by the viewer due to the pulsing.

The display 28 is a CRT, LCD, LED, projector, plasma, printer, or other display device. The display 28 displays an image or images provided in a display buffer. The rendered 3D image is displayed on the display 28. Other information, such as icons or graphics for controlling rendering, may be displayed.

Figure 3:
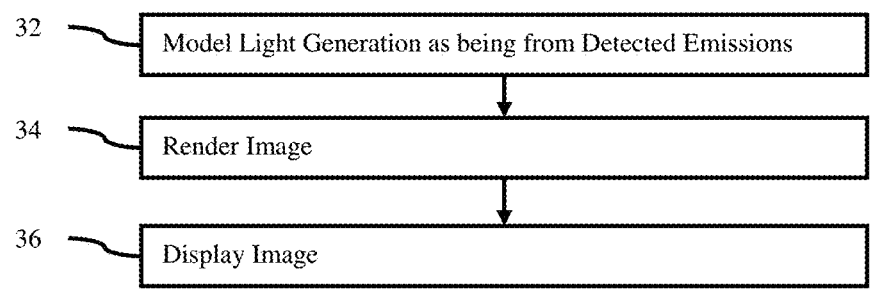
FIG. 3 is a flow chart diagram of one embodiment of a method for medical imaging from anatomical and functional information.

FIG. 3 shows one embodiment of a method for medical imaging of functional and anatomical information. To indicate the locations of and extent of biological activity or function, the rendering of the anatomy information includes the functional information. The functional information is included as lighting. The intensity and/or color of the lighting are based on the magnitude of the functional scalar. By treating the functional information as a global illumination source, the anatomy of the volume at the locations of biological activity as well as other locations is lit by the locations of biological activity. The functional information as global illumination allows various lighting cues relative to the rendered anatomy to indicate the locations of biological activity while still including anatomy other than bone with opacity (e.g., opacity between 1-75%).

The method is implemented by the system of FIG. 1 or another system. For example, acts 32 and 34 are performed by the computer 20 and/or the graphics rendering processor 26, and act 36 is performed by the display 28. Any one or more of the acts may be performed by different devices, such as the medical imager 12 or the emission imaging system 18.

The acts are performed in the order shown or other orders. For example, acts 32 and 34 are performed in the order shown, a reverse order, or simultaneously.

Additional, different, or fewer acts may be provided. For example, acts for selecting a viewing direction, window or level, transfer functions, or other rendering setting are provided. As another example, act 36 is not performed, but the image is stored or transmitted over a network.

In act 32, light is modeled as being generated by detected emissions within a patient volume. The voxels or locations for which biological activity is detected are treated as light sources. For rendering the volume, the emissions measured for functional imaging are modeled to globally illuminate the patient volume. The locations of biological activity are treated as virtual light sources within the patient volume.

The voxels of detected emissions are modeled as light sources with greater light intensity and/or specific color for greater emissions. The magnitude of the measured emissions for each voxel is mapped to the light intensity and/or color. A linear, non-linear, or other mapping may be used. The light is whiter, brighter, redder, or other characteristic for greater magnitude and darker, less intense, grayer, blacker, or other characteristic for lesser magnitude. A threshold may be applied so that light is not modeled as being generated for detected emissions below the threshold level.

The modeled lighting is added to the rendering. The anatomy is rendered using, in part, the lighting model. The lighting derived from the detected emissions (e.g., PET or SPECT scalar measures) is added to the rendering. The light is treated as emanating in multiple directions. The added light shines on or interacts with surrounding voxels in various directions. The light is added to parts of the anatomy associated with biological function, but illuminates other parts of the anatomy. For parts of the anatomy not associated with detected emissions (i.e., no biological activity or emissions below a threshold), the corresponding voxels are not treated as light sources. Light may pass through the voxels and/or interact with the voxels, but the light model does not treat the voxels as being a source of light.

The light is added using an addition function. Alternatively, the light is added using a weight of multiplication function. Other functions, such as subtractive or division, may be used to add the effects of the light model. Any light model and corresponding interaction of the light model with the volume or rendered image may be used.

The light model adds the light as having an emissive property for each location of the detected emissions. Shading, scattering, or other emissive effects from light modeled within the volume may be used. The light effect on the various voxels used for rendering is added. The rendering then uses the light model modified voxels.

Alternatively or additionally, the light model provides a light effect determined for each detector pixel or traced path. The light contribution from the light model is added to the detector pixel of the image plane once the rendering for that pixel is complete.

In act 34, a 3D image of the anatomy of the patient is generated. The anatomy representing a patient volume is rendered. The voxels of anatomy information for the volume are projected to a 2D plane. The projection uses a transfer function to map the anatomy values to display values for the voxels. The display values are accumulated along paths traced through the volume to determine the values for pixels in the 3D image. Any now known or later developed rendering operable with global illumination may be used. For example, a Monte Carlo-based rendering or light scattering approach is used.

The modeling of the light is used in the rendering. The global illumination from locations of detected emissions is included in the rendering. The added lighting results in different values for one or more of the pixels. For example, locations of detected emissions appear brighter, more intense, or tinted due to the light model. The adjacent anatomy includes shadows, intensity, tinting, and/or other characteristic to appear as if lit by the locations of detected emissions.

The rendering may include emission effects. The light model is used to modify samples transferred from the anatomy information. As the rendering accumulates samples along one or more paths for each pixel, the accumulated sample or the samples added to the accumulation are modified to account for the lighting. Alternatively, a final pixel or path value is altered to account for the light along the path.

The rendering may respond to or be controlled, in part, by the light model. For example, the light intensity along a path is accumulated. When the light intensity reaches a threshold level, the rendering along that path is terminated. The accumulated anatomy information at that point is then modified to account of the light intensity, providing the rendered pixel.

In act 36, the rendered image is displayed. The image resulting from the rendering with light modeled as being from the detected emissions is displayed. For example, a medical image representing a scanned volume is displayed. The medical image represents anatomy in a given field of view at the location in the volume. Function or biological activity of the anatomy is also represented through lighting.

Figures 4A, 4B:
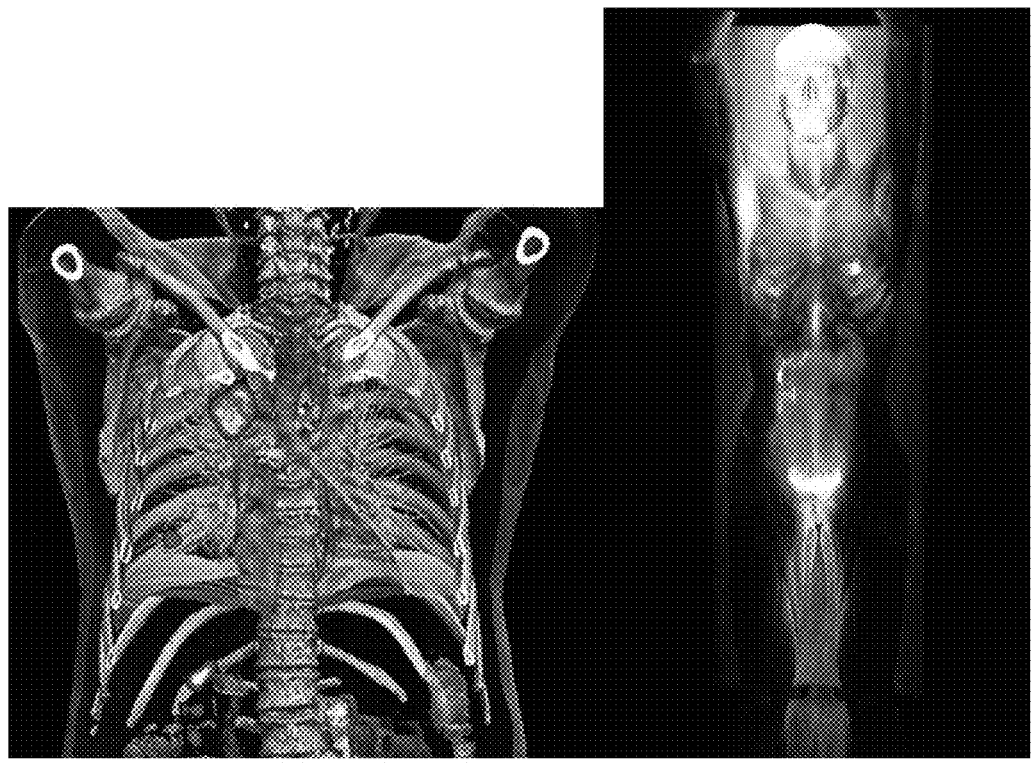
FIG. 4A is an example rendered image where a clip plane and bone transfer function are used to image functional information without occlusion. The functional information does not illuminate the volume.
FIG. 4B shows a CT volume with the only source of illumination being PET locations.

This 3D image may be used for diagnosis or other purpose. FIG. 4B shows an example rendered image with the detected emissions as light sources in global illumination. Unlike FIG. 4A, where a clip plane and bone transfer function are used to expose the functional information, FIG. 4B shows the functional information through lighting cues.

Identification of areas of increased biological activity may be more easily viewed treating them as light sources in the rendering of anatomy. The areas may be more easily viewed due to the lighting cues even if such regions are occluded by or embedded in other anatomical features. Additionally to traditional color coding, the strength of the glowing hot spots provides additional visual clues to the radiologist about the intensity of the biological activity. Instead of showing functional information inside the anatomical context using colored blobs, the functional information illuminates the surrounding anatomical features. Consequently, the areas of high metabolism are visualized as glowing hot spots illuminating the anatomy in the proximity. The light also bleeds through surrounding tissue.

The brightness and color of the light emitting areas may be directly modulated by the functional information gathered by PET and SPECT. Consequently, areas of high metabolism are easier to identify, especially in the context of photorealistic rendering of the anatomy were certain areas of functional activity might otherwise be poorly illuminated by the modeled external lighting or might be occluded by other anatomical structures. Moreover, when such light emitting areas are embedded inside soft tissue, the user is still able to identify such regions due to the light bleeding through the occluding anatomy (e.g., soft tissue). Consequently, it becomes possible to show hot spots (locations of increased emissions and/or locations of light generation) in the context of the surrounding anatomical structures without the problem of occlusion. Additionally, if external light sources are not used, the anatomical volume data may be illuminated purely by functional data.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for medical imaging of functional and anatomical information, the system comprising:
   an emission imaging system configured to measure the functional information representing a volume of a patient, wherein the emission imaging system is a positron emission tomography or a single photon emission computed tomography system;
   a medical imager configured to measure the anatomical information representing the volume of the patient, wherein the medical imager is a computed tomography or magnetic resonance system;
   a graphics rendering processor configured to render an image of the volume of the patient from the anatomical information with global illumination, the functional information designating locations of light sources for the global illumination in the rendering from the anatomical information where the global illumination transports light from the locations designated from the functional information to surrounding anatomy represented in the anatomical information; and
   a display configured to display the image of the volume of the patient.

2. The system of claim 1 wherein the functional information is a first set of voxels representing emissions from a tracer in the patient and wherein the anatomical information is a second set of voxels representing scalar measures of anatomy of the patient.

3. The system of claim 1 wherein the graphics rendering processor is configured to render the image with Monte Carlo path tracing.

4. The system of claim 1 wherein the graphics rendering processor is configured to render the image with the global illumination comprising the locations of functional information being the light sources from within the volume.

5. The system of claim 1 wherein the graphics rendering processor is configured to render the image with the global illumination comprising transporting the light to the anatomy as surrounding anatomy locations spaced from a line from a camera to a pixel location.

6. The system of claim 1 wherein the graphics rendering processor being configured to render the image comprises being configured to map an anatomy sample from the anatomical information for a location to a base color and opacity with a first transfer function and map a functional sample from the functional information for the location to a light color and light intensity with a second transfer function.

7. The system of claim 6 wherein the graphics rendering processor being configured to render the image further comprises being configured to accumulate the base color and opacity from the location and other locations along a path and modify the base color with the light color and light intensity.

8. The system of claim 7 wherein the graphics rendering processor being configured to modify comprises being configured to add the light color and light intensity as an emissive property for the location.

9. The system of claim 7 wherein the graphics rendering processor being configured to modify comprises being configured to terminate the path at the location and add the light color and light intensity to results of the accumulation for the path as terminated.

10. The system of claim 1 wherein the graphics rendering processor being configured to render comprises being configured to render a sequence of images with the global illumination varying cyclically through the sequence.

11. The system of claim 1 further comprising a user input, wherein the graphics rendering processor being configured to render with a strength of the global illumination being responsive to a control by the user from the user input.

* * * * *